United States Patent [19]

Riedel

[11] 3,993,131
[45] Nov. 23, 1976

[54] TRACING FLOW OF PETROLEUM IN UNDERGROUND RESERVOIRS

[75] Inventor: E. Frederic Riedel, Tulsa, Okla.

[73] Assignee: Cities Service Company, Tulsa, Okla.

[22] Filed: Nov. 3, 1975

[21] Appl. No.: 628,014

[52] U.S. Cl. .............................. 166/252; 23/230 EP; 73/155; 324/11
[51] Int. Cl.² .................... E21B 47/10; G01N 33/28
[58] Field of Search ............... 166/252; 23/230 EP; 73/155; 195/DIG. 11, 103.5 P; 324/.5 A, .5 AC, 2, 11

[56] References Cited
UNITED STATES PATENTS

| | | | |
|---|---|---|---|
| 2,553,900 | 5/1951 | Doan et al. | 166/252 X |
| 2,578,500 | 12/1951 | Bernard et al. | 166/252 X |
| 2,868,625 | 1/1959 | Frank | 166/252 X |
| 3,003,856 | 10/1961 | Boyd | 166/252 X |
| 3,077,387 | 2/1963 | Boyd | 23/230 EP |
| 3,112,182 | 11/1963 | Brown | 23/230 EP |
| 3,507,620 | 4/1970 | Gurney | 166/252 X |
| 3,508,875 | 4/1970 | Sandiford | 166/252 X |
| 3,508,876 | 4/1970 | Polly | 166/252 X |
| 3,740,641 | 6/1973 | Hwang et al. | 23/230 EP X |
| 3,799,261 | 3/1974 | Deans et al. | 23/230 EP X |

OTHER PUBLICATIONS

McConnell, et al., "Spin–Label Determination of Enzyme Symmetry," *The Journal of Physical Chemistry*, vol. 71, No. 1, Jan. 1967, pp. 12–14.

*Primary Examiner*—Stephen J. Novosad
*Attorney, Agent, or Firm*—Elton F. Gunn

[57] ABSTRACT

The flow path of petroleum in underground reservoirs is monitored by injecting a stable free radical, or spin label, into the reservoir as a tracer which becomes detectable in a sample taken from a producing well. Detection of the spin label is by electron spin resonance (ESR) spectroscopy. Spin label tracers are, on the average, detectable at dilutions 1 million times lower than is possible with standard chemical tracing methods.

10 Claims, No Drawings

TRACING FLOW OF PETROLEUM IN UNDERGROUND RESERVOIRS

BACKGROUND OF THE INVENTION

This invention pertains to tracing flow of fluids from a first point to a second point in an underground reservoir by injecting a small amount of a tracer material into the fluid at the first point. More particularly, this invention pertains to tracing the flow of a fluid, such as oil for example, from one point to a second point in an underground reservoir by injecting into the fluid at the first point one or more stable, free radicals, or spin labels, which are detectable by electron spin resonance analysis (ESR) to provide both quantitative and qualitative determination of the spin labels in a sample of the fluid that has been removed from the reservoir at the second point.

Both water and petroleum are produced from underground reservoirs wherein they reside in a liquid state. Efficient and economic production of such fluids is dependent upon the flow pattern thereof to a producing well site. Problems such as unexpected anisotropic permeability, unsuspected fracture orientation, uncertainty of communication between horizons, unknown stratigraphic and structural barriers, and so forth, plague the reservoir engineer faced with the task of predetermining all obstacles to efficient and economical reservoir management, yet responsible for operating a profitable fluid recovery operation. The reservoir engineer must depend, therefore, upon prompt detection and identification of problems when they do occur in order to apply remedial measures.

The need for an effective tracer system for determining flow patterns in a fluid reservoir, and the problems associated with the development of such a system, is described by Troutman and Schutz in their paper "Field Applications of Radioactive Tracers in Secondary Recovery" which appeared in *Europe and Oil*, June, 1970. They stated that a frequent manifestation of fluid flow problems in a reservoir is the appearance of an injected fluid at a producing well (second point) at a time other than that predicted. When this situation occurs, it is essential to determine the source of the injected fluid being produced, i.e. from which injection well (first point) did it come. If a different tracer chemical is added to each of several injection wells, the presence of these tracers in produced fluids will uniquely and immediately identify the injection site. In a secondary recovery process for oil, for instance, the source well of a drive fluid, such as injected water, can be determined. Accordingly, the flow pattern of oil and drive fluid to a producing well can be mapped.

To be a practical tracer, the material employed must be safe to handle and reasonable in cost. It must behave, in time of travel from the injection point to the producing point, as the fluid being traced and it must be detectable in the produced fluid, preferrable both qualitatively and quantitatively.

The use of tracer materials for tracing fluid flow in underground reservoirs is not new. Numerous materials which have been tried as tracers include various dyes; gases such as helium and carbon dioxide; acids such as picric acid, salicylic acid, ethylenediaminetetraacetic acid (EDTA), or the salts thereof; ionizable compounds which provide ammonium, boron (as borate), bromide, chromate, dichromate, iodide, nitrate or thiocynate ions; formaldehyde; carbon disulfide; and radioactive materials such as tritiated water (HTO), tritiated hydrogen (HT), tritated methane, and krypton-85.

With few exceptions, all of the previously mentioned tracer compounds have not proven to be altogether satisfactory as tracers. Other than for certain special situations, the dyes, nonradioisotopic materials, and gases are rarely used today, either because of cost considerations and/or the poor detectability thereof in the produced fluid being traced. Being detectable and measurable at concentrations as low as about $2 \times 10^{-16}$ gram-mole, the use of radioisotopes has become more accepted and is still employed, but radioactive materials have the disadvantages of being relatively expensive, in having to match the tracer type used to the fluid in the formation, in requiring specialized training and a license to assure their safe handling, and in requiring a thorough knowledge of, and availability of, sophisticated detection techniques and apparatus.

Therefore, a principle object of the present invention is to provide a tracer method for tracing fluid flow in an underground reservoir whereby the aforementioned problems associated with previous tracer methods are avoided.

One specific object of the present invention is to provide a tracer method which relies on a tracer material that is relatively low in cost, is safe, and is detectable and measurable at concentrations far lower than previously employed nonradioisotopic chemical tracers, yet which is detectable and measurable at low concentrations approaching those at which radioistropic tracers are detectable and measurable.

Another object of the present invention is to provide a tracer method which is dependent on use of tracer chemicals which are not found in nature.

SUMMARY OF THE INVENTION

In accordance with the present invention, the flow of a fluid contained in an underground reservoir is traced by injecting as a tracer a stable free radical, or spin label, into the reservoir at a first point, followed by removal of a sample of the reservoir fluid from a second point, and then analyzing the sample by electron spin resonance (ESR) spectroscopy for detecting presence of a stable free radical therein.

Stable free radicals, which are characterized in having one unpaired electron, are not found in nature as are many chemical ions and radioactive isotopes. As a consequence, the testing of the fluid sample for content of a stable free radical is not interfered with by a presence of free radicals other than those deliberately introduced into the reservoir as a tracer.

In addition, stable free radicals can be detected at concentrations as low as about $2 \times 10^{-13}$ gram-mole as opposed to about $2 \times 10^{-16}$ gram-mole for radioisotopes and about $10^{-7}$ gram-moles for standard chemical tracers. Spin labels are thus roughly $10^6$ times more detectable than standard chemical tracers and they more nearly approach the low concentration detectability of the radioisotopes. On the otherhand, the cost of spin labels can be cheaper than either the standard chemical or radioiostope methods because of lower cost of the tracer compound requirement.

DESCRIPTION OF PREFERRED AND ALTERNATIVE EMBODIMENTS

Synthetically produced, stable free radical materials, also sometimes referred to as spin labels, are both known and commercially available. See "The Application of Electron Spin Resonance and Spin-Labeling in Biochemistry and Pharmacology" by Chignell in *Aldrichimica Acta*, Vol. 7, No. 1, 1974, published by Aldrich Chemical Company, Inc. Heretofore, these materials have only been used as probes or reporter groups for biological macromolecules, and it has been necessary to effect deliberate reaction of the spin labels in order to tag the molecules so they can be traced upon moving from one point to another in the body of a living organism.

Therefore, even though spin labels have been known and available for quite some time, the general knowledge and use thereof has remained somewhat limited. Their use as tracer compounds for tracing flow of fluids in an underground reservoir has not been previously reported, and this is understandable in view of the limited knowledge of their reactability, characteristics, and behavior, and more particularly in view of the unpredictability — and frequent unreliability — of tracer usage in underground reservoirs. It has now been determined, however, that spin labels can be used as tracers in underground fluid reservoirs without need of attaching them to a molecule, and that they are not only safe and economic for use as tracers, but are also highly useful and reliable for that purpose.

Various stable free radicals can be employed as tracers when practicing the present invention. Exemplary stable free radicals include nitroxide, hydrazide and sterically hindered methyl. Preferred nitroxides include 3-Carbamoyl-2,2,5,5-tetramethyl-3-pyrrolin-1-yloxy; 3-Carbamoyl-2,2,5,5-tetramethylpyrrolidin-1-yloxy; 4-Amino-2,2,6,6-tetramethylpiperidinooxy; 4-Hydroxy-2,2,6,6-tetramethylpiperidinooxy; 4-Oxo-2,2,6,6-tetramethylpiperidinooxy. Other suitable stable free radicals of the nitroxide variety are disclosed in the aforementioned paper by Chignell. A preferred hydrozid free radical is 2,2 diphenyl-1-picrylhydrozine (DPPH) whereas a preferred sterically hindered methyl free radical is triphenylmethane.

The amount of stable free radical injected into an underground reservoir for the purpose of tracing fluid flow therein is subject to considerable variation and depends, for example, on which stable free radical is used and the volume of fluid in the reservoir. It is generally not necessary, however, to inject more than one gram-mole of the stable free radical for each 1.5 million barrels of liquid fluid in the reservoir, and in which case there can be an excess of spin labels on the order of $2.5 \times 10^4$ greater than the amount needed for reliable detection and analysis of spin labels in that volume of fluid. Greater or lesser amounts of spin labels can be injected into the reservoir where preferrable and practical.

After the spin label has been injected into an underground reservoir at a first point, samples of the reservoir fluid are periodically taken from a second point in the reservoir which is removed from the second point at a distance within the range of tens to hundreds to even thousands of feet. The samples of reservoir fluid are subjected to electron spin resonance (ESR) spectroscopy analysis to determine the time of appearance of the injected spin label at the second point in the reservoir, so that the actual time of appearance can be compared to a calculated, expected time of appearance. Any significant difference between the actual and calculated time of appearance of the spin label at the second point in the reservoir lends information regarding deviation of fluid flow therein from a suspected path of flow. Additional useful information is provided by quantitative and qualitative determination of spin labels in the sample which is made possible by the ESR analysis. ESR spectroscopy techniques are generally well known and can be used for analysis of spin label tracers in accordance with the present invention. Again, see the aforementioned paper by Chignell for discussion of ESR spectroscopy.

The preferred stable free radicals mentioned above are water soluble and can thus be advantageously employed for tracing the flow of underground water to a water well or crude oil to an oil producing well when the oil is mixed with brine and/or is driven to a producing well by means of drive fluids which comprise water, e.g. in secondary or tertiary recovery operations when water; an aqueous solution of a surfactant; or an emulsion of water, a solvent and a surfactant ("micellar solution") is injected into an oil reservoir from one or more wells as a driving fluid which pushes the crude oil toward a producing well. In such secondary or tertiary recovery operations, the spin label can be injected into the reservoir at the first point therein by dissolving it in the water or water-solvent emulsion being injected at the first point as a drive fluid. Accordingly, the spin label and its aqueous medium will leave the reservoir, in mixture with crude oil, from the second point therein by means of a producing well. However, the water containing the spin label can be readily separated from the oil of a collected sample for the purpose of conducting the necessary EST spectroscopy analysis.

As will be appreciated by those skilled in the art, secondary or tertiary recovery methods for petroleum can involve injection of water or water-containing solutions or emulsions into an underground petroleum reservoir as a drive fluid from one or more points other than the first injection point, and which are located at a distance around a second point from which petroleum is produced from the reservoir, i.e. the drive fluid can be injected into the reservoir from several injection wells located around a production well at a distance within the range of tens to thousands of feet therefrom. Accordingly, different spin labels can be injected from each of the injection wells and can be followed by ESR sepctroscopy analysis of samples taken periodically from the production well in order to determine not only the arrival of each spin label but also the amount of each spin label that arrives. By injection of several spin labels from the different wells, even more comprehensive information of fluid flow within an underground reservoir, and hence any apparent deviation from expected patterns of flow, can be determined. This is made possible by the ability of the ESR spectroscopy technique to distinguish between one spin label and another and to provide quantitive analysis of each spin label as well.

In similar fashion, a second or even a third spin level can be injected through a given injection well, at a selected time interval following injection of the first spin label, in order to determine any change in transit time to the producing well. In such fashion, any change in flow pattern of the fluid in the reservoir, between injection of one spin label and the next, can be determined.

It will be appreciated from the foregoing description that it is not necessary to react a spin label with water, oil or any other component of the reservoir fluids before the spin label can be effectively relied upon as a tracer. The spin label need only be incorporated in one or more components of the reservoir fluids at an injection well (first point), followed by migration of the fluid which contains the spin label to a production well (second point). Presence of the spin label in a component of sample liquids taken from the producing well can be determined by ESR spectroscopy whether the spin label resides within a hydrocarbon or water fraction of the sample. Accordingly, it is not essential tha the spin label be dissolved in water of the sample or that it be attached to hydrocarbon molecules of the petroleum in a sample.

Even though the present invention has been described with reference to different spin labels, tracing methods, conditions, producing methods and the like, it will nonetheless be understood that even other embodiments will become apparent which fall within the spirit and scope of the invention defined in the following claims.

What is claimed is:

1. A method for tracing the flow of fluid contained in an underground reservoir which comprises:
   a. injecting into said reservoir at a first point a stable free radical and wherein the stable free radical is injected as a tracer,
   b. removing a fluid sample from said reservoir at a second point following injection of said stable free radical, and
   c. analyzing said sample by electron spin resonance (ESR) spectroscopy for detecting presence of a stable free radical therein.

2. Method as in claim 1 wherein said tracer is injected into the reservoir while contained in water.

3. Method as in claim 2 wherein said reservoir contains liquid petroleum, a drive fluid comprising water is pumped into the reservoir through an injection well at said first point for driving the liquid petroleum toward a producing well at said second point, and wherein said tracer is incorporated within the water of said drive fluid that is pumped into the reservoir.

4. Method as in claim 1 wherein said tracer comprises a stable free radical selected from the group consisting of nitroxide, hydrazide, and sterically hindered methyl.

5. Method as in claim 1 wherein said tracer is selected from the group consisting of:
   a. 3-Carbamoyl-2,2,5,5-tetramethyl-3-pyrrolin-1-yloxy,
   b. 3-Carbamoyl-2,2,5,5-tetramethylpyrrolidin-1-yloxy,
   c. 4-Amino-2,2,6,6-tetramethylpiperidinooxy
   d. 4-Hydroxy-2,2,6,6-tetramethylpiperidinooxy,
   e. 4-Oxo-2,2,6,6-tetramethylpiperidinooxy.

6. Method as in claim 1 wherein said tracer is 2,2, diphenyl-1-picrylhydrazine (DPPH).

7. Method as in claim 1 wherein said tracer is triphenylmethane.

8. Method as in claim 1 wherein the amount of said tracer injected into said reservoir does not exceed about one gram-mole of the tracer for each 1.5 million barrels of fluid in the reservoir.

9. Method as in claim 1 wherein more than one stable free radical is injected into said reservoir at one or more points other than said first point.

10. Method as in claim 1 wherein more than one stable free radical is injected into said reservoir at said first point over one or more intervals of time.

* * * * *